(12) United States Patent
Kwon et al.

(10) Patent No.: US 8,431,660 B2
(45) Date of Patent: Apr. 30, 2013

(54) NON-METALLOCENE CATALYSTS HAVING TETRAZOL GROUP FOR OLEFIN POLYMERIZATION AND POLYMERIZING METHOD OF OLEFIN USING THE SAME

(75) Inventors: Heon-Yong Kwon, Daejeon (KR); Nicola Maggiarosa, Daejeon (KR); Ki-Soo Lee, Daejeon (KR); Min-Seok Cho, Daejeon (KR); Jong-Sang Park, Daejeon (KR); Joon-Hee Cho, Daejeon (KR); Yong-Ho Lee, Incheon (KR); Byung-Ryul Lee, Seoul (KR); Seon-Kyoung Kim, Yongin-si (KR); Dae-Sik Hong, Gunpo-si (KR)

(73) Assignee: LG Chem, Ltd., Seoul (KR)

( * ) Notice: Subject to any disclaimer, the term of this patent is extended or adjusted under 35 U.S.C. 154(b) by 361 days.

(21) Appl. No.: 12/746,441

(22) PCT Filed: Dec. 5, 2008

(86) PCT No.: PCT/KR2008/007198
§ 371 (c)(1),
(2), (4) Date: Jun. 4, 2010

(87) PCT Pub. No.: WO2009/072833
PCT Pub. Date: Jun. 11, 2009

(65) Prior Publication Data
US 2010/0256315 A1    Oct. 7, 2010

(30) Foreign Application Priority Data

Dec. 5, 2007 (KR) .................. 10-2007-0125650

(51) Int. Cl.
*C08F 4/64* (2006.01)
*C08F 4/76* (2006.01)
*C08F 4/52* (2006.01)

(52) U.S. Cl.
USPC ........... 526/161; 526/172; 526/170; 526/160; 526/131; 526/133; 526/134; 526/348; 526/348.2; 526/348.3; 526/348.5; 526/348.6; 526/351; 526/352; 502/103; 502/104; 556/51

(58) Field of Classification Search .................... 556/51; 526/172, 161, 130, 134
See application file for complete search history.

(56) References Cited

U.S. PATENT DOCUMENTS

| | | | |
|---|---|---|---|
| 6,174,975 B1 | 1/2001 | Johnson et al. | |
| 6,200,925 B1 * | 3/2001 | Ponasik et al. | 502/162 |
| 6,309,997 B1 | 10/2001 | Fujita et al. | |
| 6,747,106 B2 | 6/2004 | Wang et al. | |
| 7,705,157 B2 * | 4/2010 | Leclerc et al. | 548/101 |
| 2005/0043497 A1 * | 2/2005 | Gindelberger et al. | 526/219 |
| 2006/0094839 A1 * | 5/2006 | Diamond et al. | 526/147 |

FOREIGN PATENT DOCUMENTS

| | | |
|---|---|---|
| CN | 1345322 A | 4/2002 |
| CN | 1390867 A | 1/2003 |
| CN | 101045765 A | 10/2007 |
| CN | 101092459 A | 12/2007 |
| JP | 2005-513136 A | 5/2005 |

OTHER PUBLICATIONS

Meyer, E.; Zucco, C.; Gallardo, H., J. Mater. Chem., 1998, 8, 1351-1354.*

* cited by examiner

*Primary Examiner* — Rip A. Lee
(74) *Attorney, Agent, or Firm* — McKenna Long & Aldridge, LLP

(57) ABSTRACT

The present invention provides a non-metallocene transition metal compound that is easily produced, includes a tetrazol group having the high polymerization activity and high temperature stability in the polymerization of olefins, and a catalytic composition that includes the transition metal compound and a cocatalyst. In addition, the present invention provides a method for efficiently producing an olefin homopolymer or copolymer by using the catalytic composition.

17 Claims, No Drawings

NON-METALLOCENE CATALYSTS HAVING TETRAZOL GROUP FOR OLEFIN POLYMERIZATION AND POLYMERIZING METHOD OF OLEFIN USING THE SAME

This application is a 35 U.S.C. §371 National Stage entry of International Application No. PCT/KR2008/007198, filed on Dec. 5, 2008, and claims priority to Korean Application No. 10-2007-0125650, filed on Dec. 5, 2007, which are all hereby incorporated by reference in their entireties.

TECHNICAL FIELD

The present invention relates to a catalyst for polymerizing non-metallocene olefin using a transition metal compound including a tetrazol group, a method for producing the same, and a method for producing an olefin polymer using the catalyst for polymerizing the olefin. This application claims priority from Korean Patent Application No. 10-2007-0125650 filed on Dec. 5, 2007 in the KIPO, the disclosure of which is incorporated herein by reference in its entirety.

BACKGROUND ART

The product ion and the application of polyolefins have been greatly developed in conjunction with the invention of a catalyst that is called Ziegler-Natta catalyst, and production processes and purposes of products have been developed in various fields. In particular, as the activity of the Ziegler-Natta catalyst is largely improved, polyolefin products using various single active point catalysts are developed in the art. Examples of the single active point catalyst include a metallocene catalyst, a Constrained-Geometry-Catalyst (CGC) of Dow, Co., Ltd., and catalysts using late transition metals.

In the copolymerization reaction of ethylene and alpha-olefin, excellent characteristics that the CGC has, as compared with (per se) known metallocene catalysts can be usually classified into the two categories: (1) it produces a high molecular weight polymer with high activity even at a high polymerization temperature, and (2) it yields very excellent copolymerization of an alpha-olefin having high steric hindrance, such as 1-hexene and 1-octene. In addition, upon polymerization reaction, several characteristics of CGC have been gradually noticed, and thus extensive studies to synthesize a derivative of CGC for use as a polymerization catalyst have been made in the academic and industrial fields.

As one approach, there have been trials for synthesis of metal compounds to which various bridges and nitrogen substituents instead of silicon bridges are introduced, and polymerization using the same. Some representative examples of recently known metal compounds include the following compounds 1 to 4 (Chem. Rev. 2003, 103, 283):

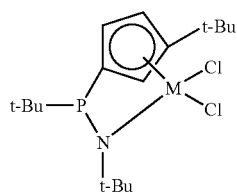
(1)

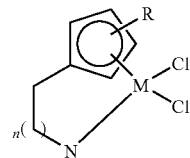
(2)

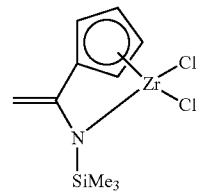
(3)

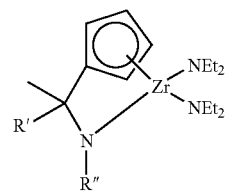
(4)

To the above-listed compounds 1 to 4, a phosphorous bridge (1), an ethylene or propylene bridge (2), a methylidene bridge (3), and a methylene bridge (4) are each introduced, instead of the silicon bridges in the CGC structure. However, when they are used for ethylene polymerization, or copolymerization with an alpha-olefin, they had no excellent results regarding the activity or the copolymerization performances, as compared with CGC.

As another approach, there have been trials for synthesis of many compounds comprising an oxido ligand instead of the amido ligand of the CGC, and sometimes polymerization using the same. Examples thereof are summarized as follows:

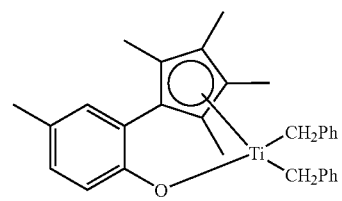
(5)

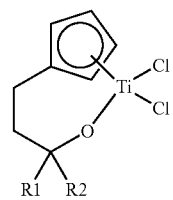
(6)

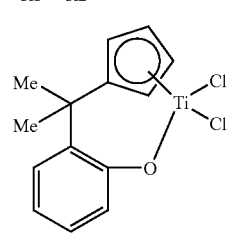
(7)

-continued

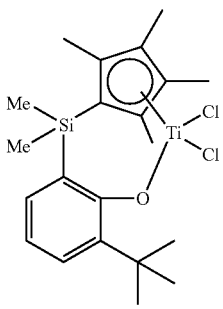

(8)

The compound (5) is characterized in that a Cp (cyclopentadiene) derivative and an oxido ligand are bridged via an ortho-phenylene group, as disclosed by T. J. Marks, et al. (Organometallics 1997, 16, 5958). Also, a compound having the same bridge and polymerization using the same are disclosed by Mu, et al. (Organometallics 2004, 23, 540). Further, an indenyl ligand and an oxido ligand are bridged via an ortho-phenylene group, as disclosed by Rothwell, et al. (Chem. Commun. 2003, 1034). The compound (6) is characterized in that a cyclopentadienyl ligand and oxido ligand are bridged through three carbons, as disclosed by Whitby, et al. (Organometallics 1999, 18, 348), but these catalysts are reported to exhibit activity on syndiotactic polystyrene polymerization. Further, similar compounds are also reported by Hessen, et al. (Organometallics 1998, 17, 1652).

The compound (7) is characterized in that it exhibits activity on ethylene polymerization and ethylene/1-hexene copolymerization at a high temperature and a high pressure (210° C., 150 MPa), as disclosed by Rau, et al. (J. Organomet. Chem. 2000, 608, 71). Further, synthesis of a catalyst having the similar structure (8), and polymerization at a high temperature and a high pressure were filed in the patent application by Sumitomo (U.S. Pat. No. 6,548,686).

It is reported that a ligand that has two cyclopentadiene-type anion frames shows high activity in the case of when a catalyst in which a transition metal compound (hereinafter, referred to as "metallocene") of Group 4 of the periodic table and methyl aluminoxane or the specific boron compound are used as a cocatalyst is used to polymerize olefins. In addition, it is reported that a polymer having a narrow molecular weight distribution and composition distribution is produced, which is commercially advantageous.

In addition, in non-metallocene systems, in 1999, Fujita, T. et al. of Mitsui Chemicals, Co., Ltd. introduced a salicylaldimine ligand in which various substituents are present in an amine element, and announced in EP 0874005 that the ligand is a catalyst system having the very high polymerization activity to olefins such as ethylene, propylene and the like. In the same year, they announced in JP11-158189 that a transit ion metal of Group 4 is introduced into a hydroxybenzylamine ligand by reducing the salicylaldimine ligand, thus the ligand is a catalyst system showing the polymerization activity to olefins.

In addition, it is reported that in a catalyst for polymerizing, which includes a transition metal compound of Group 4 of the periodic table having one cyclopentadiene-type anion frame and a ligand where the frame and a nitrogen atom are crosslinked with each other by a silicon group and methylaluminoxane or a specific boron compound, in the polymerization of olefins, a polymer having the high molecular weight is produced with high activity (Japanese Unexamined Patent Application Publication No. 1991-163088, and Japanese Unexamined Patent Application Publication No. 1991-188092). However, the transition metal compound, particularly, in the case of when it has a crosslinking structure, synthesis of the ligand is difficult to perform, a plurality of processes is required, and a complexation process is not easily carried out.

However, among the above catalysts for polymerizing olefins, only few catalysts are substantially in use for commercial plants. Thus, there is still a need of development of a catalyst having a novel structure, and production of a polymer using the same. Particularly, the conventional binuclear catalyst compounds still have structures in the CGC form, and the method for producing the same is complex and the product ion yield is low. Therefore, there is still a desire of a binuclear transition metal compound having a novel structure, which is capable of exhibiting a catalytic activity, and a method for simply producing the same in high yield.

DISCLOSURE

Technical Problem

It is an object of the present invention to provide a non-metallocene transition metal compound that is easily produced, includes a tetrazol group having the high polymerization activity and high temperature stability in the polymerization of olefins, and a catalytic composition that includes the transition metal compound and a cocatalyst. In addition, it is another object of the present invention to provide a method for efficiently producing an olefin homopolymer or copolymer by using the catalytic composition.

Technical Solution

In order to accomplish the above objects, the present invention provides a transit ion metal compound which is represented by the following Formula 1:

[Formula 1]

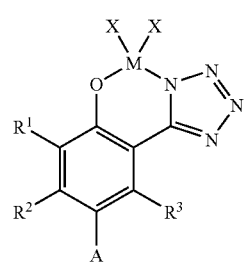

wherein $R^1$ to $R^3$ are each independently a hydrogen atom; alkyl having 1 to 20 carbon atoms; aryl that is substituted or unsubstituted by a fluoroalkyl, nitro, sulfonate or halogen group and having 6 to 20 carbon atoms; alkenyl having 2 to 20 carbon atoms; alkylaryl having 7 to 20 carbon atoms; arylalkyl having 7 to 20 carbon atoms; a halogen group; a nitro group; a sulfonate group; a siloxyl group (—$OSiZ_3$, where Z is an aryl group having 6 to 12 carbon atoms or an alkyl group having 1 to 12 carbon atoms); or a hydrocarbylene group (—$(RO)zR'$, where R is an alkylene group having 2 to 12 carbon atoms or an arylene group having 6 to 12 carbon atoms, R' is an alkyl group having 1 to 12 carbon atoms and an aryl group having 6 to 20 carbon atoms, and z is in the range of 1 to 4), and $R^1$ and $R^2$ may be connected to each other to form a ring, A represents an electron donor group, Xs may be the same as or different from each other, and a halogen group, an alkyl group having 1 to 20 carbon atoms, an allyl group, a benzyl group, a nitro group, an amido group ($-N(R)_2$), an alkylsilyl group having 1 to 20 carbon atoms, an alkoxy group having 1 to 20 carbon atoms, a sulfonate group, or a derivative thereof, and M may be selected from Groups 3 to 11 transition metals of the periodic table.

In particular, it is preferable that $R^1$ is a substituent having a high steric hindrance, such as aryl and a derivative thereof, a branched-chained alkyl group having 3 to 6 carbon atoms, an alkoxyalkyl group, phenyl, an anthracyl group, a penanthracyl group, terphenyl and tert-butyl.

In addition, in the hydrocarbylene group (—(RO)zR'), it is preferable that R is an alkylene group having 2 to 3 carbon atoms, and a phenyl group, and it is preferable that R' is hydrocarbon having 1 to 3 carbon atoms.

In addition, it is preferable that A is selected from the group consisting of a hydrogen atom, $NO_2$, a halogen group, a persulfonate ($SO_3^-$) group, sulfonyl ester ($SO_2R$), a carboxyl group (COO—), a perfluoroalkyl group, an alkoxy group, and carboxylate and sulfonate that includes cations of alkali metal or alkali earth metal.

In addition, it is preferable that M is a Group 4 transition metal such as titanium, zirconium and hafnium.

As another embodiment of the present invention, there is provided a method for producing the transition metal compound of the Formula 1. The method comprises the steps of adding a compound including a transition metal to a reaction solution that includes a compound including tetrazol and a strong basic compound such as butyl lithium (n-BuLi).

As another embodiment of the present invention, there is provided a catalytic composition for polymerizing olefins, which includes a) the transition metal compound according to Formula 1 and b) at least one cocatalyst compound selected from the group consisting of compounds that are represented by the following Formulas 2 to 4:

$$-[Al(R^4)-O]_a- \qquad \text{[Formula 2]}$$

wherein $R^4$ is each independently a halogen radical; a hydrocarbyl radical having 1 to 20 carbon atoms; or a hydrocarbyl radical that is substituted by halogen and has 1 to 20 carbon atoms;

a is an integer of 2 or more;

$$J(R^5)_3 \qquad \text{[Formula 3]}$$

wherein J is aluminum or boron; $R^5$ is each independently a halogen radical, a hydrocarbyl radical having 1 to 20 carbon atoms, or a hydrocarbyl radical that is substituted by halogen and has 1 to 20 carbon atoms;

$$[L-H]^+[Z(R^6)_4]^- \text{ or } [L]^+[Z(R^6)_4]^- \qquad \text{[Formula 4]}$$

wherein L is a neutral or cationic Lewis acid; H is a hydrogen atom; Z is a Group 13 element; $R^6$ is each independently an aryl or alkyl radical having 6 to 20 carbon atoms in which one or more hydrogen atoms are substituted by halogen, hydrocarbyl having 1 to 20 carbon atoms, or an alkoxy or phenoxy radical.

In addition, the present invention provides a method for producing a catalytic composition, which comprises the steps of a) contacting the transition metal compound of the Formula 1 and a compound that is represented by the Formula 2 or 3 to each other to obtain a mixture; and b) adding the compound of the Formula 4 to the mixture obtained in step a).

In addition, the present invention provides a method for producing a catalytic composition, which comprises the step of contacting the transition metal compound of the Formula 1 and a compound that is represented by the Formula 2 to each other to obtain a mixture.

In addition, the present invention provides a method for producing a catalytic composition, which comprises the step of contacting the transition metal compound of the Formula 1 and a compound that is represented by the Formula 4 to each other to obtain a mixture.

In addition, the present invention provides a method for producing polyolefins, which comprises the steps of contacting the catalytic composition and an olefin monomer to each other.

Advantageous Effects

According to the present invention, the catalytic composition comprising a novel structure of a Group 4 transition metal compound and having the high activity and copolymerization property can be used to produce a polyolefin having a high molecular weight.

BEST MODE

Hereinafter, the present invention will be described in detail.

A transition metal compound that is represented by Formula 1 according to the present invention is a novel compound, and may be used as a catalyst for polymerizing polyolefins.

As described in the following Reaction Equation 1, the transition metal compound may be produced by adding a transition metal to a reaction solution that includes a compound including tetrazol and a strong basic compound such as butyl lithium (n-BuLi).

As the strong basic compound, at least one of an alkyllithium compound, NaH and KH may be used.

In the reaction solution and the transition metal for producing the transition metal compound, the molar ratio of the compound including tetrazol:the strong basic compound:the transition metal may be 1:1~3:0.5~2 and preferably 1:2:1.

[Reaction Equation 1]

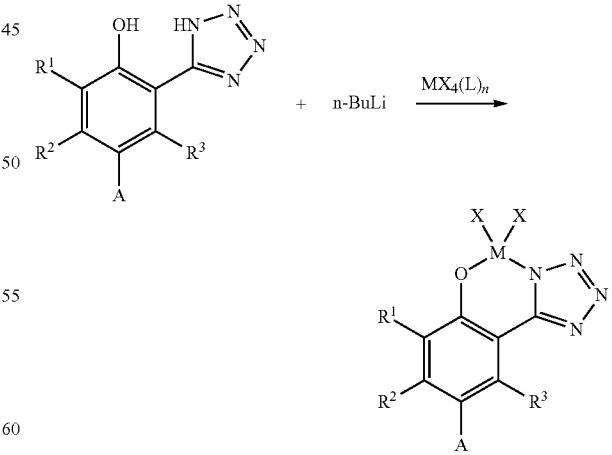

wherein $R^1$, $R^2$, $R^3$, A, M, and X are the same as those defined in Formula 1, and in $MX_4(L)n$, L is an electron donor ligand, and n is an integer in the range of 0 to 10.

Preferably, illustrative, but non-limiting examples of the electron donor ligand include tetrahydrofurane (THF).

The catalytic composition according to the present invention is present in an activation state by the react ion between the transit ion metal compound and the cocatalysts, and may be used in an olefin single polymerization or copolymerization.

Firstly, the present invention provides a method for producing the catalytic composition, comprising the steps of: a) contacting a transition metal compound of the Formula 1 and a compound represented by the Formula 2 or 3 to obtain a mixture; and b) adding a compound represented by the Formula 4 to the mixture obtained in the a) step.

In addition, secondly, the present invention provides a method for producing the catalytic composition, comprising a step of contacting a transition metal compound of the Formula 1 and a compound represented by the Formula 2 to obtain a mixture.

In addition, thirdly, the present invention provides a method for producing the catalytic composition, comprising a step of contacting a transition metal compound of the Formula 1 and a compound represented by the Formula 4 to obtain a mixture.

In the first method among the methods for producing the catalytic composition, the molar ratio of the transition metal compound of the Formula 1 and the compound represented by the Formula 2 or 3 is preferably 1:1 to 1:5,000, more preferably 1:2 to 1:1,000, and most preferably 1:5 to 1:500. In the case of when the molar ratio is in the above range, since the amount of the alkylating agent is sufficient, the alkylating of the metal compound may be completely carried out, and side reactions between the remaining alkylating agent in the excessive amount and an activating agent of Formula 4 may be minimized. Thus, the activation of the alkylated metal compound may be completely carried out.

Next, the molar ratio of the transition metal compound of the Formula 1 and the compound represented by the Formula 4 is preferably 1:1 to 1:50, more preferably 1:1 to 1:25, and most preferably 1:2 to 1:10. In the case of when the molar ratio is in the above range, since the amount of the activation agent is sufficient, the activation of the transition metal compound may be completely performed, thus the activity of the produced catalytic composition is not reduced and the amount of the remaining activation agent is minimized. Accordingly, the cost of the catalytic composition is economic and the purity of the polymer is not reduced.

After X of the transit ion metal compound is first alkylated by using the activation agent of Formula 2 or Formula 3 by the above method, the catalytic composition may be produced by forming complexes with boron and the like by using the activation agent of Formula 4.

In the second method for producing the catalytic composition, the molar ratio of the transition metal compound of the Formula 1 and the compound represented by the following Formula 2 is preferably 1:10 to 1:10,000, more preferably 1:100 to 1:5,000, and most preferably 1:500 to 1:2000. In the case of when the molar ratio is in the above range, since the amount of the activation agent is sufficient, the activation of the metal compound may be completely performed, thus the activity of the produced catalytic composition is not reduced and the amount of the remaining activation agent is minimized. Accordingly, the cost of the catalytic composition is economic and the purity of the produced polymer is not reduced.

In addition, in the third method for producing the catalytic composition, the molar ratio of the transition metal compound of the Formula 1 and the compound represented by the following Formula 4 is preferably 1:1 to 1:50, more preferably 1:1 to 1:25, and most preferably 1:2 to 1:10. In the case of when the molar ratio is in the above range, since the amount of the activation agent is sufficient, the activation of the transition metal compound may be completely performed, thus the activity of the produced catalytic composition is not reduced and the amount of the remaining activation agent is minimized. Accordingly, the cost of the catalytic composition is economic and the purity of the produced polymer is not reduced.

In the production of the catalytic composition, as the reaction solvent, a hydrocarbon solvent such as pentane, hexane and heptane, or an aromatic solvent such as benzene and toluene can be used, but not limited thereto. All of the solvents available in the art can be used.

In addition, the transition metal compound of the Formula 1 and the cocatalysts may be used as supported on silica or alumina, and the supporting method may be a method that is known in the art to which the present invention belongs.

The compound represented by represented by the Formula 2 is not particularly limited as long as it is alkyl aluminoxane, and preferable examples thereof include methyl aluminoxane, ethyl aluminoxane, isobutyl aluminoxane and butyl aluminoxane, among which methyl aluminoxane is a particularly preferred compound.

The alkyl metal compound represented by the Formula 3 is not particularly limited, and preferable examples thereof include trimethyl aluminum, triethyl aluminum, triisobutyl aluminum, tripropyl aluminum, tributyl aluminum, dimethylchloro aluminum, triisopropyl aluminum, tri-s-butyl aluminum, tricyclopentyl aluminum, tripentyl aluminum, triisopentyl aluminum, trihexyl aluminum, trioctyl aluminum, ethyldimethyl aluminum, methyldiethyl aluminum, triphenyl aluminum, tri-p-tolyl aluminum, dimethyl aluminum methoxide, dimethyl aluminum ethoxide, trimethyl boron, triethyl boron, triisobutyl boron, tripropyl boron, and tributyl boron, among which a particularly preferred compound is selected from trimethyl aluminum, triethyl aluminum, and triisobutyl aluminum.

Examples of the compound represented by represented by the Formula 4 include triethyl ammonium tetra(phenyl) boron, tributyl ammonium tetra(phenyl) boron, trimethyl ammonium tetra(phenyl) boron, tripropyl ammonium tetra(phenyl) boron, trimethyl ammonium tetra(p-tolyl) boron, trimethyl ammonium tetra(o,p-dimethyl phenyl) boron, tributyl ammonium tetra(p-trifluoromethyl phenyl) boron, trimethyl ammonium tetra(p-trifluoromethyl phenyl) boron, tributyl ammonium tetra(pentafluoro phenyl) boron, N,N-diethyl anilinium tetra(phenyl) boron, N,N-diethyl anilinium tetra(phenyl) boron, N,N-diethyl anilinium tetra(pentafluorophenyl) boron, diethyl ammonium tetra(pentafluorophenyl) boron, triphenyl phosphonium tetra(phenyl) boron, trimethyl phosphonium tetra(phenyl) boron, tripropyl ammonium tetra(p-tolyl) boron, triethyl ammonium tetra(o,p-dimethyl phenyl) boron, N,N-diethyl anilinium tetra(phenyl) boron, triphenyl carbonium tetra(p-trifluoromethyl phenyl) boron, triphenyl carbonium tetra(pentafluorophenyl) boron, trityltetra(pentafluorophenyl) boron, triethyl ammonium tetra(phenyl) aluminum, tributyl ammonium tetra(phenyl) aluminum, trimethyl ammonium tetra(phenyl) aluminum, tripropyl ammonium tetra(phenyl) aluminum, trimethyl ammonium tetra(p-tolyl) aluminum, tripropyl ammonium tetra(p-tolyl) aluminum, triethyl ammonium tetra(o,p-dimethyl phenyl) aluminum, tributyl ammonium tetra(p-trifluoromethyl phenyl) aluminum, trimethyl ammonium tetra(p-trifluoromethyl phenyl) aluminum, tributyl ammonium tetra (pentafluorophenyl) aluminum, N,N-diethyl anilinium tetra (phenyl) aluminum, N,N-diethyl anilinium tetra(phenyl) aluminum, N,N-diethyl anilinium tetra(pentafluorophenyl)

aluminum, diethyl ammonium tetra(pentafluorophenyl) aluminum, triphenyl phosphonium tetra(phenyl) aluminum, trimethyl phosphonium tetra(phenyl) aluminum, triethyl ammonium tetra(phenyl) aluminum, and tributyl ammonium tetra(phenyl) aluminum.

In addition, the present invention provides a method for producing a polyolefin using the catalytic composition. Specifically, the present invention provides a method for producing a polyolefin which comprises a step of contacting the catalytic composition and at least one olefin monomer.

In the method for producing a polyolefin according to the present invention, solution process is the most preferable polymerization process which is using the catalytic composition. In addition, the catalytic composition also can be applied to slurry or gas-phase process when an inorganic support such as silica is used together.

In the method for producing a polyolefin according to the present invention, the catalytic composition can be diluted with or dissolved in solvents that are suitable for an olefin polymerization process, prior to injection. The solvent may be an aliphatic hydrocarbon solvent having 5 to 12 carbon atoms, such as pentane, hexane, heptane, nonane, decane, and isomers thereof; an aromatic hydrocarbon solvent such as toluene and benzene; or a hydrocarbon solvent substituted with chlorine such as dichloromethane and chlorobenzene. The solvent used herein is preferably used after removing a small amount of water, air, etc. which functions as a catalyst poison, by treatment with a small amount of alkyl aluminum, and a cocatalyst can be additionally used therefor.

Examples of the olefin monomers which are polymerizable with the transition metal compounds and the cocatalysts include ethylene, alpha-olefins and cyclic olefins, and diene olefin monomers or triene olefin monomers having two or more double bonds. Specific examples of the monomers include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, and 3-chloromethylstyrene, and two or more kinds of the monomers can be mixed for copolymerization. In the present invention, among the above monomers, preferred is at least one monomer selected from ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-itocene.

The polyolefin produced according to the method of the present invention may be either of a homopolymer and a copolymer. If the polyolefin is a copolymer made from the comonomer other than ethylene, the monomers constituting the copolymer is preferably ethylene, and at least one monomer selected from propylene, 1-butene, 1-hexene, 4-methyl-1-pentene, and 1-octene.

In particular, in the method for producing the olefin polymer according to the present invention, the catalytic composition is capable of being subjected to the copolymerization reaction of ethylene with the monomer having the large steric hindrance such as 1-octene, at a reaction temperature that is used in the related art, at a high reaction temperature of 90° C. or higher, or even at a reaction temperature of 140° C. or higher. By introducing various substituents into a substituent group having a hetero atom such as an amine group and an imine group, electronic and steric environments around the metal may be easily controlled, and ultimately, the structure and physical properties of the produced polyolefin may be control led.

MODE FOR INVENTION

Hereinbelow, the present invention will be described in detail with reference to Examples. The present invention may, however, be embodied in many different forms and should not be construed as being limited to the Examples set forth herein.

Example

The organic reagent and the solvent were purchased from Aldrich Chemical Company and Merck limited, and purified using a standard method for use. In all the steps for synthesis, contact with air and the moisture was avoided to increase the reproductivity of the experiments. In order to demonstrate the structure of the compound, 400 MHz Nuclear Magnetic Resonance (NMR) spectrometer was used.

The melting point (Tm) of the polymer was determined using a DSC (Differential Scanning Calorimeter) 2920 manufactured by TA Instruments. That is, the temperature was raised to 200° C., maintained at that temperature for 5 minutes, lowered to 30° C., and then raised, and thereafter the peak of the DSC curve was taken as a melting point. At that time, the temperature raising and lowering rates were 10° C./min and the melting point was obtained during the second temperature elevation.

Example 1

Production of
3,5-Di-tert-butyl-2-hydroxybenzonitrile

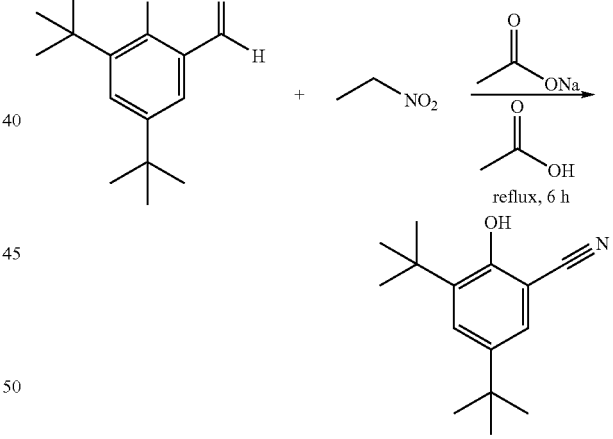

[Reaction Equation 2]

By using the following method, like Reaction Equation 2, 3,5-Di-tert-butyl-2-hydroxybenzo nitrile was produced.

The mixture of 3,5-di-tert-butyl-2-hydroxybenzaldehyde (9.38 g, 40 mmol), nitroethane (5.75 mL, 6.0 g, 80 mmol), anhydrous sodium acetate (6.56 g, 80 mmol), and a glacial acetic acid (10 mL) was put into the 250 ml flask, and refluxed for 12 hours at 120° C. After that, they were cooled to normal temperature, and 80 ml distilled water and 40 ml ethyl acetate were put into the reaction mixture, and extracted twice. The separated organic layer was washed twice by using 40 ml sodium bicarbonate saturated aqueous solution, and the water layer was removed. After that, the separated organic layer was dried by using anhydrous magnesium sulfate. The obtained crude product was dissolved in petroleum ether and recrystallized at a low temperature (−15° C.) to obtain a yellow solid (yield: 6.40 g, m.p.: 120-121° C.).

$^1$NMR (500 MHz, CDCl$_3$, ppm): d=1.29 (s, 9H), 1.41 (s, 9H), 6.12 (broad s, 1H), 7.30 (d, J 52.4 Hz, 1H), 7.50 (d, J 52.4 Hz, 1H).

$^{13}$C NMR (500 MHz, CDCl$_3$, ppm): d=29.3 (3C), 31.2 (3C), 34.4, 35.2, 99.5, 117.4, 126.1, 129.8, 137.2, 143.5, 155.0. 2

Example 2

Production of 2,4-di-tert-butyl-6-(1H-tetrazol-5-yl)phenol

[Reaction Equation 3]

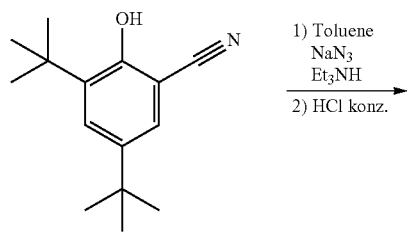

1) Toluene
   NaN$_3$
   Et$_3$NH
2) HCl konz.

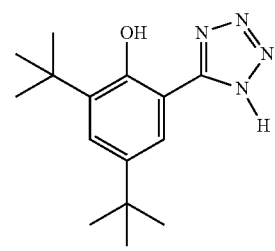

By using the following method, like Reaction Equation 3, 2,4-di-tert-butyl-6-(1H-tetrazol-5-yl)phenol was produced.

Into the flask, 3,5-di-tert-butyl-2-hydroxybenzonitrile (39.3 g, 0.17 mol), sodium azide (11.1 g, 0.17 mol) and ammonium triethyl chloride (23.3 g, 0.17 mol) were put, and dissolved in 400 ml anhydrous toluene. The reaction solution was refluxed at 105° C. for 2 days. After the reaction was finished, the solvent was removed under vacuum, 250 ml distilled water and 35 wt % hydrochloric acid were added in a small amount, and HN$_3$ that was generated under reduced pressure was removed to obtain a white precipitate. This white precipitate was washed with water, and the white solid was separated through the filter and dried under a reduced pressure to obtain a tetrazol compound. The tetrazol compound was recrystallized in 60% methanol aqueous solution to be purified (40 g, 0.146 mol, 86%).

$^{13}$C NMR (500 MHz, CDCl$_3$, ppm): d=31.3 (3C), 31.9 (3C), 35.5, 41.7, 117.9, 124.5, 125.0, 138.4, 142.9, 145.9, 163.7

Example 3

Production of 2,4-di-tert-butyl-6-(1H-tetrazol-5-yl)phenoxy titanium chloride

[Reaction Equation 4]

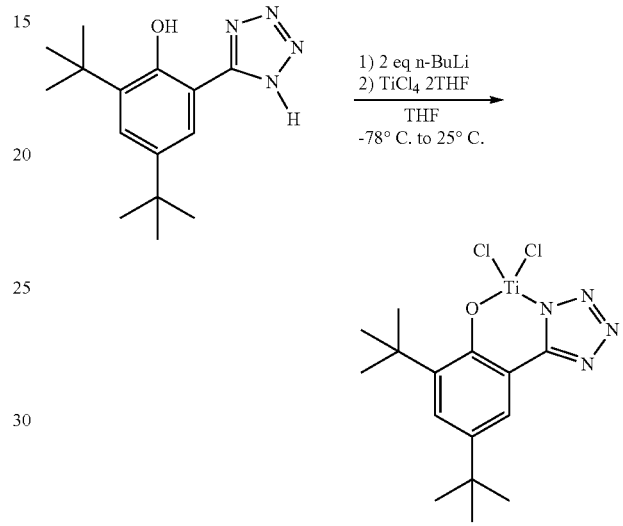

1) 2 eq n-BuLi
2) TiCl$_4$ 2THF

THF
−78° C. to 25° C.

By using the following method, like Reaction Equation 4, 2,4-di-tert-butyl-6-(1H-tetrazol-5-yl) phenoxy titanium chloride was produced.

Into the flask, 2,4-di-tert-butyl-6-(1H-tetrazol-5-yl)phenol (13.72 g, 50 mmol) and the THF solvent in the amount of 200 mL were put and cooled to −78° C. After that, 2 equivalents of n-BuLi (2.5M in Hexane, 0.1 mol, 50 mL) were slowly dropped, and agitated at normal temperature for 6 hours. To the reaction mixture solution, TiCl$_4$(THF)$_2$ (16.7 g, 50 mmol) was added. The solution was agitated for 6 hours and the reaction was finished. After that, the solvent was removed under a vacuum, and 150 ml hexane was added thereto to carryout the filtration. The filtered solution was recrystallized under a low temperature, and the solid precipitate was separated through the filter, and dried under a reduced pressure to obtain a desired compound (14.7 g, 75%).

$^{13}$C NMR (500 MHz, CDCl$_3$, ppm): d=31.2, 31.3 (3C), 31.7 (3C), 41.5, 117.8, 124.0, 124.8, 137.4, 142.8, 149.3, 165.5

Example 4

Ethylene Homopolymerization Using the Produced Catalyst (1)

Into the pressure reactor under a high purity argon atmosphere, 250 mL of purified toluene and 2.93 mL of 4.6 wt % methyl aluminoxane toluene solution (manufactured by Albemarle, Co., Ltd.) as the cocatalyst were injected, and heated to the temperature of 60° C. 5 mL of the toluene solution (5 mmol of Ti) in which the non-metallocene polymerization catalyst obtained in Example 3 was dissolved was added thereto and agitated. After that, the polymerization started while ethylene at 50 psig was added to the reactor. After it was agitated for 30 min, the agitation was stopped and the pressure was reduced. To the polymerization device, 10 wt % hydrochloric acid-ethanol solution was added, the polymerization was stopped, and the filtration was carried out to obtain the white solid precipitate. The precipitate was washed by using ethanol and dried at 60° C. in a vacuum oven for 24 hours to produce the final ethylene polymer. The reaction condition and physical properties of the produced polymer are described in the following Table 1.

Example 5

Ethylene Homopolymerization Using the Produced Catalyst (2)

The ethylene polymer was produced by using the same method as Example 4, except that the polymerization was performed at the polymerization temperature of 80° C. The reaction condition and physical properties of the produced polymer are described in the following Table 1.

Example 6

Ethylene/1-hexene Copolymerization Using the Produced Catalyst (1)

Into the pressure reactor under a high purity argon atmosphere, 250 mL a purified toluene and 2.93 mL of 10 wt % methyl aluminoxane toluene solution (manufactured by Albemarle, Co., Ltd.) as the cocatalyst were injected, and heated to the temperature of 60° C. 5 mL of the toluene solution (5 mmol of Ti) in which the non-metallocene polymerization catalyst obtained in Example 3 was dissolved and 10 mL of the 1-hexene solution were added thereto and agitated. After that, the polymerization started while ethylene at 50 psig was added to the reactor. After it was agitated for 30 min, the agitation was stopped and the pressure was reduced. To the polymerization device, 10 wt % hydrochloric acid-ethanol solution was added, the polymerization was stopped, and the filtration was carried out to obtain the white solid precipitate. The precipitate was washed by using ethanol and dried at 60° C. in a vacuum oven for 24 hours to produce the final ethylene/1-hexene copolymer. The reaction condition and physical properties of the produced polymer are described in the following Table 1.

Example 7

Ethylene/1-hexene Copolymerization Using the Produced Catalyst (2)

The ethylene/1-hexene copolymer was produced by using the same method as Example 6, except that the polymerization was performed at the polymerization temperature of 80° C. The reaction condition and physical properties of the produced copolymer are described in the following Table 1.

TABLE 1

| run[a] | polymerizaion temperature (° C.) | 1-hexene (mL) | Mn[b] (×10⁻³) | Mw/Mn[b] | Tm[c] (° C.) | Yield (g) |
|---|---|---|---|---|---|---|
| 1 | 60 | — | 475 | 2.1 | 129.4 | 3.4 |
| 2 | 60 | 10 | 394 | 3.0 | 117.3 | 3.8 |
| 3 | 80 | — | 557 | 2.2 | 132.2 | 4.8 |
| 4 | 80 | 10 | 421 | 2.8 | 119.1 | 5.0 |

Example 8

Production of 5-(2-hydroxyphenyl)-1H-tetrazol

[Reaction Equation 5]

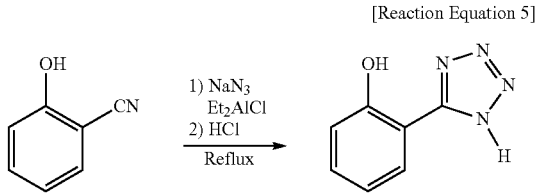 [SMILES: N#Cc1ccccc1O ; Oc1ccccc1-c1nnn[nH]1]

Into the flask, 100 mL of anhydrous toluene and diethyl aluminum chloride (40 mmol, 1.8 M toluene solution) were put and cooled to 0° C. Sodium azide (2.6 g, 40 mmol) was put into the mixture, and the mixture was agitated at room temperature for 4 hours. After the agitated solution was cooled to 0° C. again, 2-hydroxybenzonitrile (20 mmol, 2.38 g) was added thereto. The reaction mixture was refluxed at 80 for 1 day. After the reaction was finished, the mixture was cooled to 0° C., 70 mL of 6 M HCL, 50 mL of distilled water, 100 mL of ethyl acetate, and 80 mL of saturated NaCl were dropped thereon, treated, and extracted. The organic phase was reextracted by using 200 mL of water twice. The combined water layers were extracted with 200 mL of ethyl acetate twice. The combined organic layers were dried through $Na_2SO_4$. The solvent was removed to obtain the product. The product was recrystallized from ethyl acetate to obtain a pure product (yield 80%).

Example 9

Production of 2-(1H-tetrazol-5-yl) phenoxy titanium dichloride

[Reaction Equation 6]

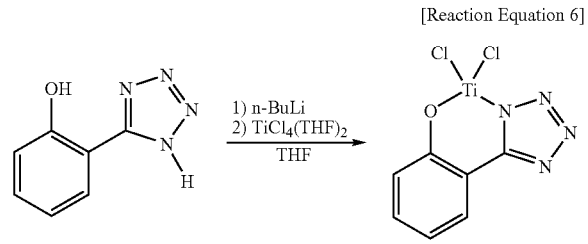

Into the flask, 5-(2-hydroxyphenyl)-1H-tetrazol (3.24 g, 20 mmol) that was produced in Example 8 and 100 mL of the THF solvent were put and cooled to −78° C. After that, 2 equivalents of n-BuLi (2.5 M in Hexane, 40 mmol, 16 mL) were slowly dropped, and agitated at normal temperature for 6 hours. To the reaction mixture solution, $TiCl_4(THF)_2$ (6.67 g, 20 mmol) was added. The solution was agitated for 6 hours and the reaction was finished. After that, the solvent was removed under vacuum, and 100 ml methylene chloride was added thereto to carry out the filtration. The filtered solution was recrystallized under a low temperature, and the solid precipitate was separated through the filter, and dried under a reduced pressure to obtain a desired compound (70%).

$^{13}$C NMR (500 MHz, CDCl$_3$, ppm): δ=116.4, 123.0, 123.3, 135.9, 143.8, 150.1, 160.2

Example 10

Ethylene Homopolymerization Using the Produced Catalyst (3)

The ethylene polymer was produced by using the same method as Example 4, except that the polymerization was performed by using the catalyst that was produced in Example 9. The reaction condition and physical properties of the produced polymer are described in the following Table 2.

Example 11

Ethylene/1-hexene Copolymerization by Using the Produced Catalyst (2)

The ethylene/1-hexene copolymer was produced by using the same method as Example 6, except that the polymerization was performed by using the catalyst that was produced in Example 9. The reaction condition and physical properties of the produced polymer are described in the following Table 2.

TABLE 2

| run$^a$ | polymerizaion temperature (° C.) | 1-hexene (mL) | Mn$^b$ (×10$^{-3}$) | Mw/Mn$^b$ | Tm$^c$ (° C.) | yield (g) |
| --- | --- | --- | --- | --- | --- | --- |
| 1 | 60 | — | 475 | 2.1 | 129.4 | 3.4 |
| 2 | 60 | 10 | 394 | 3.0 | 117.3 | 3.8 |
| 3 | 80 | — | 557 | 2.2 | 132.2 | 4.8 |
| 4 | 80 | 10 | 421 | 2.8 | 119.1 | 5.0 |
| 5 | 80 | — | 210 | 3.1 | 133.2 | 1.3 |
| 6 | 80 | 10 | 150 | 3.5 | 115.2 | 1.5 |

Polymerization condition $^a$ethylene pressure (50 psig), polymerization time (60 min), cocatalyst MAO (Al/Ti = 1000), and toluene (250 mL)

$^b$measurement by using gel permeation chromatography (GPC)

$^c$measurement by using differential scanning calorimeter (DSC)

INDUSTRIAL APPLICABILITY

A catalytic composition according to the present invention that comprises a novel structure of a Group 4 transition metal compound and has the high activity and copolymerization property can be used to produce a polyolefin having a high molecular weight.

The invention claimed is:

1. A transition metal compound which is represented by the following Formula 1:

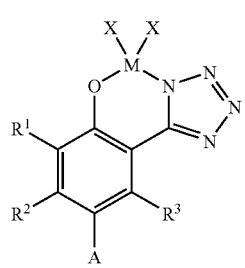

[Formula 1]

wherein R$^1$ to R$^3$ are each independently a hydrogen atom; alkyl having 1 to 20 carbon atoms; aryl that is unsubstituted or substituted by a fluoroalkyl, nitro, sulfonate or halogen group and having 6 to 20 carbon atoms; alkenyl having 2 to 20 carbon atoms; alkylaryl having 7 to 20 carbon atoms; arylalkyl having 7 to 20 carbon atoms; a halogen group; a nitro group; a sulfonate group; a siloxyl group (—OSiZ$_3$, where Z is an aryl group having 6 to 12 carbon atoms or an alkyl group having 1 to 12 carbon atoms); or a hydrocarbylene group (—(RO)zR', where R is an alkylene group having 2 to 12 carbon atoms or an arylene group having 6 to 12 carbon atoms, R' is an alkyl group having 1 to 12 carbon atoms and an aryl group having 6 to 20 carbon atoms, and z is in the range of 1 to 4), and R$^1$ and R$^2$ may be connected to each other to form a ring, A is selected from the group consisting of a hydrogen atom, a branched-chained alkyl group having 3 to 6 carbon atoms, NO$_2$, a halogen group, a persulfonate (SO$_3^-$) group, sulfonyl ester (SO$_2$R), a carboxyl group (COO—), a perfluoroalkyl group, an alkoxy group, and carboxylate and sulfonate that includes cations of alkali metal or alkali earth metal, Xs may be the same as or different from each other, and is halogen group, an alkyl group having 1 to 20 carbon atoms, an allyl group, a benzyl group, a nitro group, an amido group (—N(R)$_2$), an alkylsilyl group having 1 to 20 carbon atoms, an alkoxy group having 1 to 20 carbon atoms, or a sulfonate group, and M is a Group 4 transition metal selected from the group consisting of titanium, zirconium and hafnium.

2. The transition metal compound as set forth in claim 1, wherein R$^1$ is selected from the group consisting of aryl and a derivative thereof, a branched-chained alkyl group having 3 to 6 carbon atoms, an alkoxyalkyl group, phenyl, an anthracyl group, terphenyl and tert-butyl.

3. A method for producing the transition metal compound according to claim 1, wherein the transition metal compound is produced by adding a transition metal to a reaction solution that includes a compound including tetrazol and a strong basic compound:

[Reaction Equation 1]

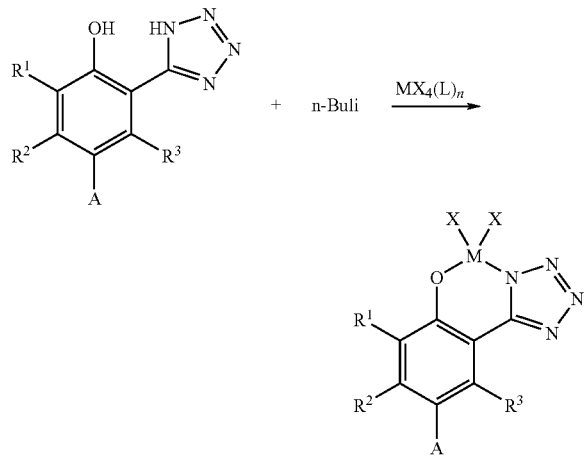

wherein R¹, R², R³, A, M, and X are the same as those defined in the Formula 1, in MX₄(L)n, L represents an electron donor ligand, and n is an integer in the range of 0 to 10.

4. The method for producing the transition metal compound as set forth in claim 3, wherein the electron donor ligand (L) is tetrahydrofuran (THF).

5. The method for producing the transition metal compound as set forth in claim 3, wherein the strong basic compound is one selected from the group consisting of an alkyllithium compound, NaH and KH.

6. A catalytic composition for polymerizing olefins, comprising a) the transition metal compound according to claim 1 and b) at least one cocatalyst compound selected from the group consisting of compounds that are represented by the following Formulas 2 to 4;

—[Al(R⁴)—O]ₐ—  [Formula 2]

wherein R⁴ is each independently a halogen radical; a hydrocarbyl radical having 1 to 20 carbon atoms; or a hydrocarbyl radical that is substituted by halogen and has 1 to 20 carbon atoms;
a is an integer of 2 or more;

J(R⁵)₃  [Formula 3]

wherein J is aluminum or boron; R⁵ is each independently a halogen radical, a hydrocarbyl radical having 1 to 20 carbon atoms, or a hydrocarbyl radical that is substituted by halogen and has 1 to 20 carbon atoms;

[L-H]⁺[Z(R⁶)₄]⁻ or [L]⁺[Z(R⁶)₄]⁻  [Formula 4]

wherein [L-H]⁺ and [L]⁺ are cationic Lewis acids, and L is the corresponding conjugate base of these acids; H is a hydrogen atom; Z is a Group 13 element; R⁶ is each independently an aryl or alkyl radical having 6 to 20 carbon atoms in which one or more hydrogen atoms are substituted by halogen, hydrocarbyl having 1 to 20 carbon atoms, or an alkoxy or phenoxy radical.

7. The catalytic composition for polymerizing olefins as set forth in claim 6, wherein the compound of the Formula 2 is selected from the group consisting of methyl aluminoxane, ethyl aluminoxane, isobutyl aluminoxane and butyl aluminoxane.

8. The catalytic composition for polymerizing olefins as set forth in claim 6, wherein the compound of the Formula 3 is selected from the group consisting of trimethyl aluminum, triethyl aluminum, triisobutyl aluminum, tripropyl aluminum, tributyl aluminum, dimethylchloro aluminum, triisopropyl aluminum, tri-s-butyl aluminum, tricyclopentyl aluminum, tripentyl aluminum, triisopentyl aluminum, trihexyl aluminum, trioctyl aluminum, ethyldimethyl aluminum, methyldiethyl aluminum, triphenyl aluminum, tri-p-tolyl aluminum, trimethyl boron, triethyl boron, triisobutyl boron, tripropyl boron, and tributyl boron.

9. The catalytic composition for polymerizing olefins as set forth in claim 6, wherein the compound of the Formula 4 is selected from the group consisting of triethyl ammonium tetra(phenyl) boron, tributyl ammonium tetra(phenyl) boron, trimethyl ammonium tetra(phenyl) boron, tripropyl ammonium tetra(phenyl) boron, trimethyl ammonium tetra(p-tolyl) boron, trimethyl ammonium tetra(o,p-dimethyl phenyl) boron, tributyl ammonium tetra(p-trifluoromethyl phenyl) boron, trimethyl ammonium tetra(p-trifluoromethyl phenyl) boron, tributyl ammonium tetra(pentafluorophenyl) boron, N,N-diethyl anilinium tetra(phenyl) boron, N,N-diethyl anilinium tetra(pentafluorophenyl) boron, diethyl ammonium tetra(pentafluorophenyl) boron, triphenyl phosphonium tetra(phenyl) boron, trimethyl phosphonium tetra(phenyl) boron, tripropyl ammonium tetra(p-tolyl) boron, triethyl ammonium tetra(o,p-dimethyl phenyl) boron, triphenyl carbonium tetra(p-trifluoromethyl phenyl) boron, triphenyl carbonium tetra(pentafluorophenyl) boron, triethyl ammonium tetra(phenyl) aluminum, tributyl ammonium tetra(phenyl) aluminum, trimethyl ammonium tetra(phenyl) aluminum, tripropyl ammonium tetra(phenyl) aluminum, trimethyl ammonium tetra(p-tolyl) aluminum, tripropyl ammonium tetra(p-tolyl) aluminum, triethyl ammonium tetra(o,p-dimethyl phenyl) aluminum, tributyl ammonium tetra(p-trifluoromethyl phenyl) aluminum, trimethyl ammonium tetra(p-trifluoromethyl phenyl) aluminum, tributyl ammonium tetra(pentafluorophenyl) aluminum, N,N-diethyl anilinium tetra(phenyl) aluminum, N,N-diethyl anilinium tetra(phenyl) aluminum, N,N-diethyl anilinium tetra(pentafluorophenyl) aluminum, diethyl ammonium tetra(pentafluorophenyl) aluminum, triphenyl phosphonium tetra(phenyl) aluminum, trimethyl phosphonium tetra(phenyl) aluminum, triethyl ammonium tetra(phenyl) aluminum, and tributyl ammonium tetra(phenyl) aluminum.

10. A method for producing a catalytic composition, the method comprising the steps of:
a) contacting the transition metal compound according to claim 1 and a compound that is represented by the following Formula 2 or 3 to each other to obtain a mixture; and
b) adding the compound of the following Formula 4 to the mixture obtained in step a):

—[Al(R⁴)—O]ₐ—  [Formula 2]

wherein R⁴ is each independently a halogen radical; a hydrocarbyl radical having 1 to 20 carbon atoms; or a hydrocarbyl radical that is substituted by halogen and has 1 to 20 carbon atoms;
a is an integer of 2 or more;

J(R⁵)₃  [Formula 3]

wherein J is aluminum or boron; R⁵ is each independently a halogen radical, a hydrocarbyl radical having 1 to 20 carbon atoms, or a hydrocarbyl radical that is substituted by halogen and has 1 to 20 carbon atoms;

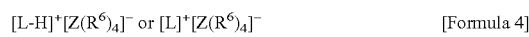
[L-H]⁺[Z(R⁶)₄]⁻ or [L]⁺[Z(R⁶)₄]⁻  [Formula 4]

wherein [L-H]⁺ and [L]⁺ are cationic Lewis acids, and L is the corresponding conjugate base of these acids; H is a hydrogen atom; Z is a Group 13 element; $R^6$ is each independently an aryl or alkyl radical having 6 to 20 carbon atoms in which one or more hydrogen atoms are substituted by halogen, hydrocarbyl having 1 to 20 carbon atoms, or an alkoxy or phenoxy radical.

11. The method for producing a catalytic composition as set forth in claim 10, wherein the molar ratio of the transition metal compound and the compound that is represented by the Formula 2 or Formula 3 is in the range of 1:1 to 1:5,000, and the molar ratio of the transition metal compound and the compound that is represented by the Formula 4 is in the range of 1:1 to 1:50.

12. A method for producing a catalytic composition, wherein the method comprises the step of contacting the transition metal compound according to claim 1 and a compound that is represented by the following Formula 2 to each other to obtain a mixture:

—[Al($R^4$)—O]$_a$—      [Formula 2]

wherein $R^4$ is each independently a halogen radical, a hydrocarbyl radical having 1 to 20 carbon atoms, or a hydrocarbyl radical that is substituted by halogen and has 1 to 20 carbon atoms; and a is an integer of 2 or more.

13. The method for producing a catalytic composition as set forth in claim 12, wherein the molar ratio of the transition metal compound and the compound that is represented by the Formula 2 is in the range of 1:10 to 1:10,000.

14. A method for producing a catalytic composition, wherein the method comprises the step of contacting the transition metal compound according to claim 1 and a compound that is represented by the following Formula 4 to each other to obtain a mixture:

[L-H]$^+$[Z($R^6$)$_4$]$^-$ or [L]$^+$[Z($R^6$)$_4$]$^-$      [Formula 4]

wherein [L-H]$^+$ and [L]$^+$ are cationic Lewis acids, and L is the corresponding conjugate base of these acids; H is a hydrogen atom; Z is a Group 13 element; $R^6$ is each independently an aryl or alkyl radical having 6 to 20 carbon atoms in which one or more hydrogen atoms are substituted by halogen, hydrocarbyl having 1 to 20 carbon atoms, or an alkoxy or phenoxy radical.

15. The method for producing a catalytic composition as set forth in claim 14, wherein the molar ratio of the transition metal compound and the compound that is represented by the Formula 4 is in the range of 1:1 to 1:50.

16. A method for producing polyolefins, wherein the method comprises the step of contacting the catalytic composition according to claim 6 and an olefin monomer to each other.

17. The method for producing polyolefins as set forth in claim 16, wherein the olefin monomer includes one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, and 3-chloromethylstyrene.

\* \* \* \* \*